United States Patent [19]

Haber et al.

[11] Patent Number: 5,511,538
[45] Date of Patent: Apr. 30, 1996

[54] SUPER ATOMIZING NONCHLORINATED FLUOROCARBON MEDICATION INHALER

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 120,691

[22] Filed: Sep. 13, 1993

Related U.S. Application Data

[63] Continuation of Ser. No. 924,358, Jul. 31, 1992, abandoned, which is a continuation of Ser. No. 551,990, Jul. 12, 1990, abandoned.

[51] Int. Cl.$^6$ ................................ A61M 11/00
[52] U.S. Cl. ................ 128/200.14; 128/200.18; 128/200.22
[58] Field of Search .......... 128/200.14, 200.18, 128/200.22

[56] References Cited

U.S. PATENT DOCUMENTS

| | | | |
|---|---|---|---|
| 238,388 | 3/1881 | Heine | 128/200.22 |
| 460,458 | 9/1891 | Bates | 128/200.14 |
| 905,087 | 11/1908 | Mallory | 128/200.22 |
| 923,822 | 6/1909 | Dorment | 128/200.22 |
| 1,838,873 | 12/1931 | Scott | 128/200.22 |
| 2,079,587 | 5/1937 | Aronson | 128/200.22 |
| 3,144,867 | 8/1964 | Trupp et al. | 128/200.22 |
| 3,155,573 | 11/1964 | Fowler | 128/200.22 |
| 4,405,308 | 9/1983 | Jessup | 128/200.22 |
| 4,923,448 | 5/1990 | Ennis, III | 128/200.22 |

OTHER PUBLICATIONS

McGraw–Hill Encyclopedia of Science & Technology, Atomization, pp. 858–862.

*Primary Examiner*—Aaron J. Lewis
*Attorney, Agent, or Firm*—Townsend and Townsend and Crew

[57] ABSTRACT

An atomizing inhaler (2) includes a body (4) having a hollow interior (10) with an elastomeric barrier (22) at the tip (6) of the body. The elastomeric barrier has a slit (104) formed through the barrier. A pressurized liquid inhalant is atomized as it is forced out through the slit into the ambient environment in mist or smaller sized drops. The body includes a spring-biased piston (40) which moves within a cylinder (32). The cylinder and piston together define a variable volume container (33). The volume of the variable volume container varies according to the position of the piston within the cylinder. The liquid in the variable volume container is pressurized by the piston and flows through the slit in the barrier. The invention is broadly directed to an atomizer which uses an elastomeric barrier having a slit formed therein so that applying pressurized liquid to one side of the barrier causes the pressurized liquid to atomize as passes through the slit to mist or smaller sized drops.

15 Claims, 3 Drawing Sheets

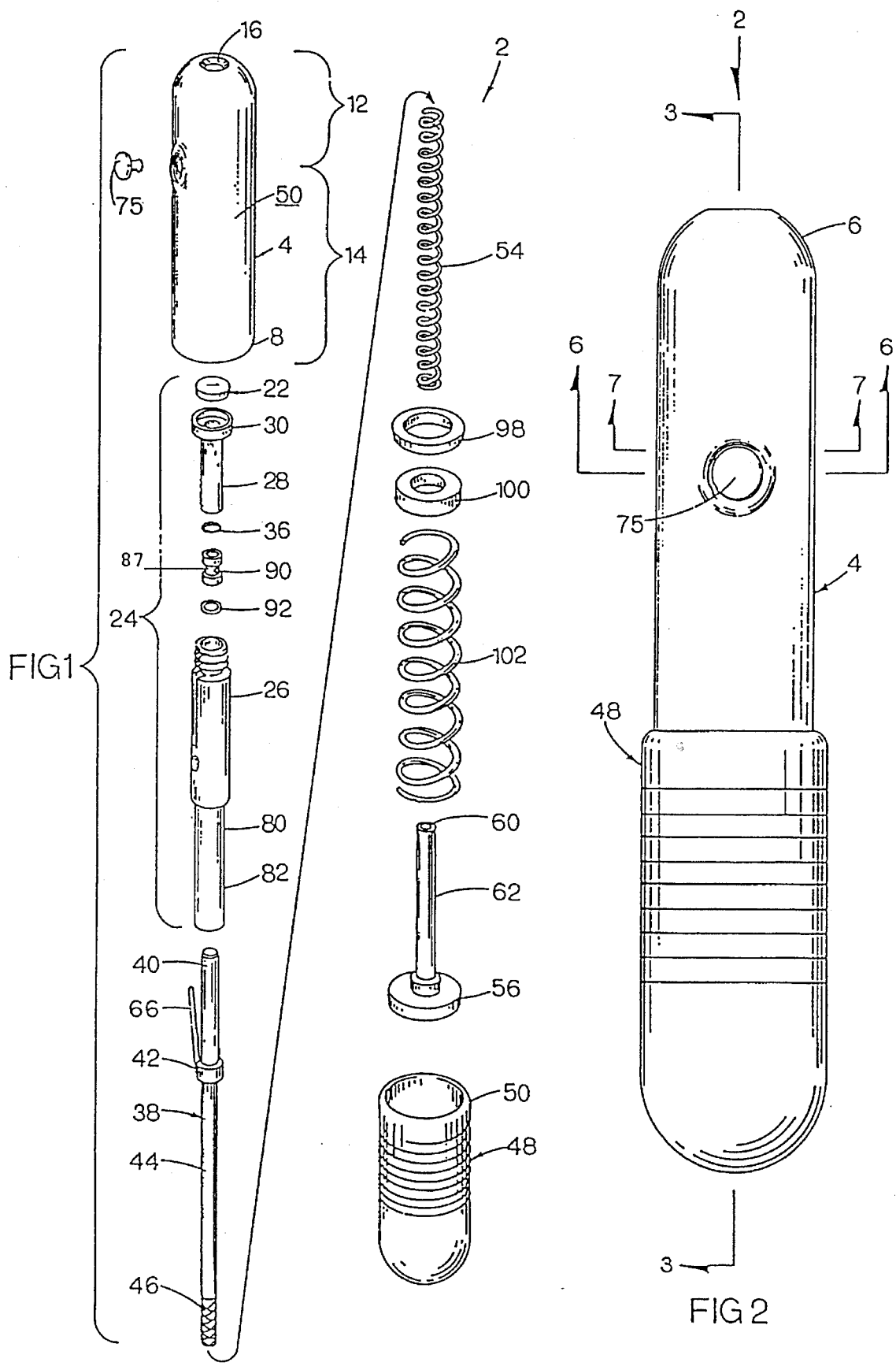

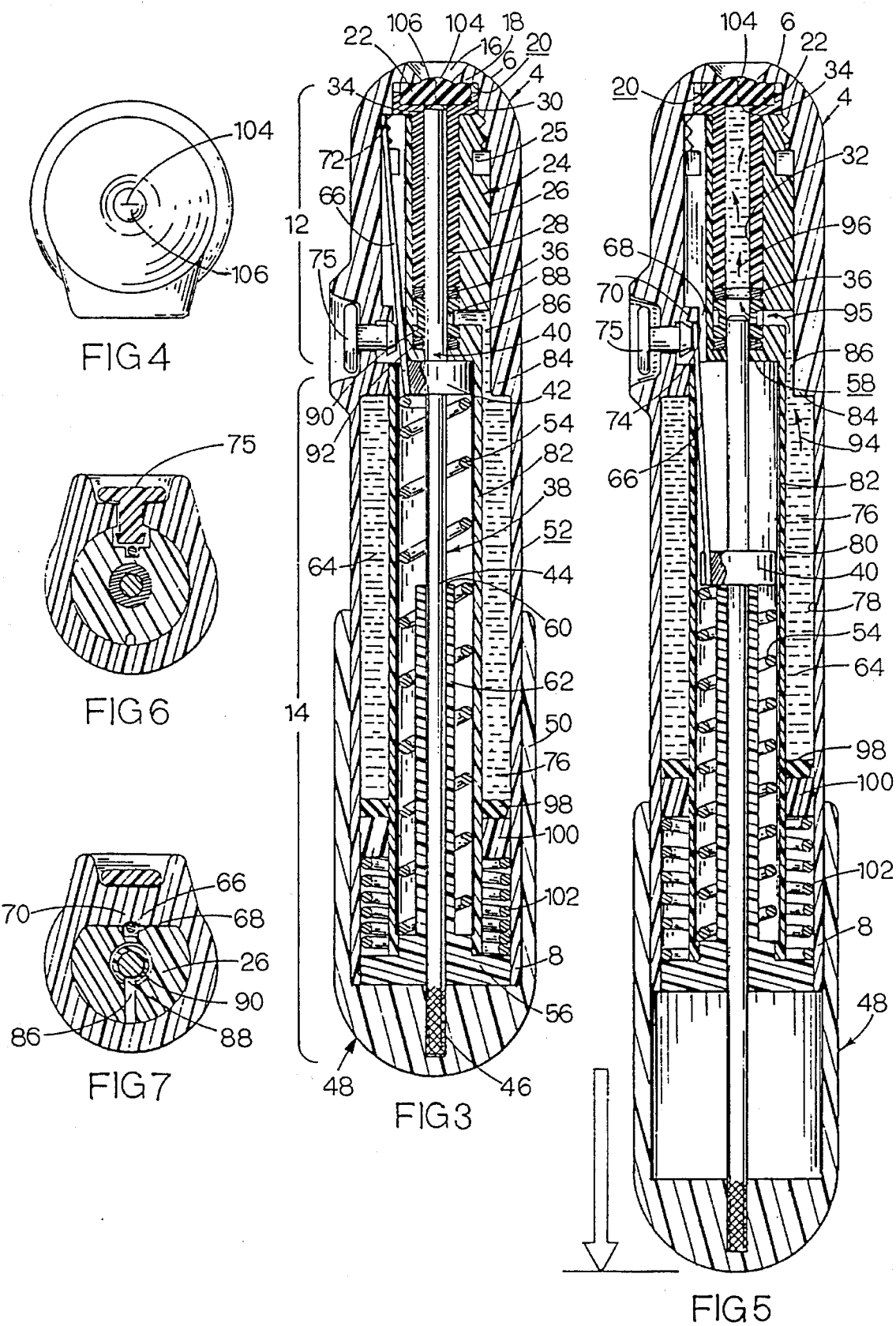

SUPER ATOMIZING NONCHLORINATED FLUOROCARBON MEDICATION INHALER

This is a Continuation of application Ser. No. 07/924,358, filed Jul. 31, 1992, now abandoned, which is a Continuation of application Ser. No. 07/551,990, filed Jul. 12, 1990, now abandoned.

BACKGROUND OF THE INVENTION

Atomization is the mechanical subdivision of liquid into drops. Although the terminology is not standard, drops can be broken into several size categories. Spraying creates coarse drops in the range of 100–1,000 microns in diameter. A mist is typically considered to be fine drops in the 10–100 micron range while nebulizing creates very fine drops under 10 microns in diameter. Nebulized liquids are generally preferred in inhalation aerosol therapy.

To produce the very fine drops desired for inhalation therapy, prior art inhalers generally use a gas propellant. Although these gas-powered inhalers work well, they result in the release of the propellants into the atmosphere. Some of these propellants may be chlorinated fluorocarbons which are known to be quite damaging to the ozone layer. Hydrocarbons are also used, but are also not beneficial to the atmosphere. In addition, some hydrocarbons may react adversely with some medications.

SUMMARY OF THE INVENTION

The present invention is directed broadly to a mechanical atomizer which atomizes a liquid to fine or very fine drop size using a nozzle formed as a slit through an elastomeric material.

The mechanical atomizer is, in one preferred embodiment, in the form of an atomizing inhaler. The inhaler includes a body having a hollow interior with an elastomeric barrier at the tip of the body. The elastomeric barrier has a slit formed through the barrier. A liquid under pressure is forced out through the slit into the ambient environment. The barrier is configured so that the liquid is atomized as it passes through the slit in the barrier and passes into the ambient environment as fine or very fine drops.

The body preferably includes a piston and cylinder arrangement by which the liquid in the cylinder is pressurized by the piston and flows through the slit in the barrier. The piston is movable between a retracted position, against the bias of a piston drive spring, at which the piston is at least substantially withdrawn from the cylinder, and a discharged position, at which the piston is in its full engagement position within the cylinder. The piston is moved from the discharged position to the retracted position by pulling on a cap connected to the piston by a piston extension. The cap is coaxial with the body. When the piston is in the retracted position, the piston may be temporarily maintained in the retracted position through the engagement of a resilient arm, carried by piston with a catch, mounted to the body. The resilient arm is spring biased radially outwardly so that the end of the arm moves into engagement with the radially extending catch when in the retracted position. The arm is released from the catch by pressing on a trigger or button which permits the piston drive spring to force the piston down the cylinder, thus causing the liquid within the cylinder to be forced out through the slit in the barrier.

The inhaler also includes an axially extending annular reservoir positioned between the outer wall of the body and an inner wall of a sleeve housing the piston and piston spring. The body includes a pathway fluidly coupling the reservoir with the interior of the cylinder when the piston is in the retracted position. The pathway is sealed as the piston moves from the retracted position towards the discharge position, thus trapping the liquid within the cylinder so that movement of the piston along the cylinder can only occur by the discharge of the liquid through the slit.

Movement of the piston from the discharged position to the retracted position creates a partial vacuum within the cylinder. The liquid within the reservoir is urged through the pathway and into the cylinder by this partial vacuum and also by a coil spring biased ring seal. The ring seal is positioned for axial movement along the axially extending annular reservoir and provides a relatively small pressure on the liquid to help ensure that the cylinder is filled or substantially filled with the liquid after each cycling of the piston.

A primary advantage of the present invention is that it permits the creation of fine and/or very fine drops of liquid using a relatively simple nozzle design without requiring extremely high liquid pressures. Although the present invention is particularly suited for inhalation therapy, in its broader form it may be used for other purposes, such as misting vegetables in grocery stores or creating a cool outdoor environment in hot, dry climates. Also, the present invention eliminates the need to use gas propellants, thus eliminating any contamination problems with the liquid inhalant which could otherwise be created. Also, deleterious effects on the atmosphere, caused by through the use of gas propellants, are also avoided with the invention.

Other features and advantages of the invention will appear from the following description in which the preferred embodiments have been set forth in detail in conjunction with the accompanying drawings.

BRIEF DESCRIPTION OF THE DRAWINGS

FIG. 1 is an exploded isometric view of an atomizing inhaler made according to the invention;

FIG. 2 is an assembled view of the inhaler of FIG. 1;

FIG. 3 is a cross-sectional view taken along line 3—3 of FIG. 2;

FIG. 4 is a top plan view of the inhaler of FIG. 2;

FIG. 5 is a cross-sectional of the inhaler of FIG. 3 shown in the retracted position;

FIG. 6 is a cross-sectional view of the inhaler of FIG. 2 taken along line 6—6;

FIG. 7 is a cross-sectional view of the inhaler of FIG. 2 taken along the line 7—7.

DESCRIPTION OF THE PREFERRED EMBODIMENTS

Figure 8:
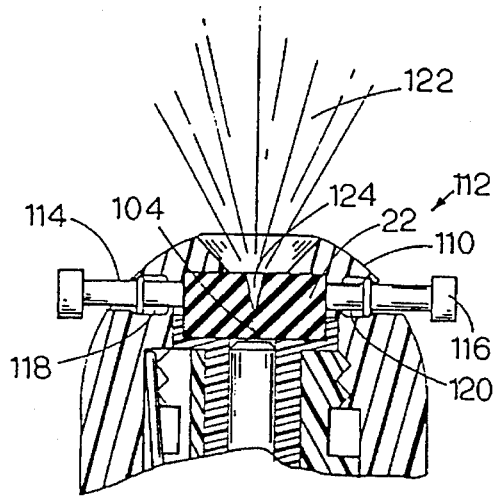
FIGS. 8–11 are cross-sectional views illustrating the tip of an inhaler similar to the inhaler of FIG. 3 but with spray deflector buttons which can be used to angle the spray, as in FIGS. 9 & 10, or narrow the spray, as in FIG. 11, from the normal spray pattern of FIG. 8.
Figure 9:
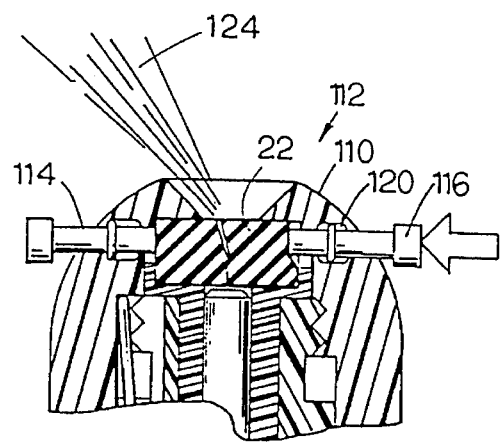
Figure 10:
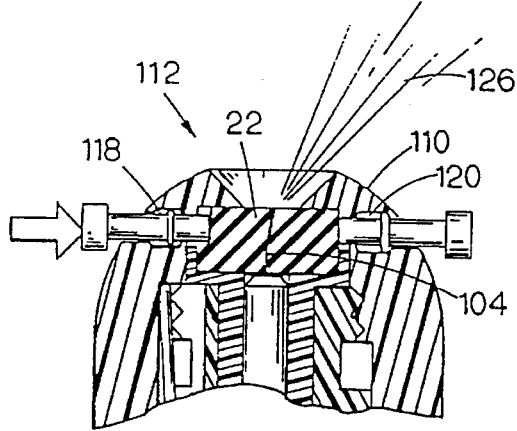
Figure 11:
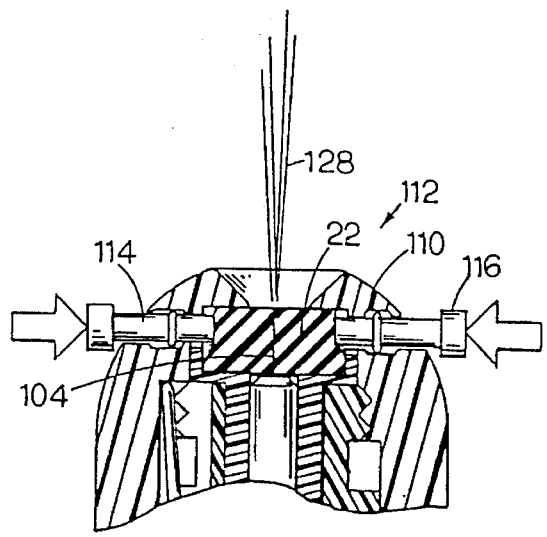

FIG. 1 illustrates an atomizing inhaler 2 made according to the invention in an exploded form while FIGS. 2 and 3 illustrate the inhaler of FIG. 1 assembled and in its at-rest or discharged position. Inhaler 2 includes a hollow, cylindrical body 4 ending in a tip 6 at one end and a base end 8 at the other. Interior 10 of body 4 is generally divided into a forward region 12 and a rearward region 14. Forward region 12 includes a tip opening 16 at tip 6 defining a ledge 18.

Ledge 18 has an inner surface 20 against which an elastomeric barrier 22 is positioned. Barrier 22 is secured against surface 20 by a cylinder assembly 24 threadably mounted at 25 within forward region 12 of interior 10. Cylinder assembly 24 includes an outer, plastic housing 26 and an inner sleeve 28 having a cup-shaped end 30 which presses against barrier 22. Sleeve 28 defines an accurately sized cylindrical bore 32 shown in FIG. 5. In the preferred embodiment, cylindrical bore 32 has a bore diameter of 2 mm and a bore length sufficient to provide a 10 mm stroke as measured from the end 34 of bore 32 to a first O-ring 36 at the other end of bore 32.

A piston assembly 38 is mounted for axial movement within interior 10 of body 4. Assembly 38 includes a piston 40 sized for close, sliding fit within cylindrical bore 32. Cylindrical bore 32 and piston 40 together define a variable volume container 33. The volume of variable volume container 33 varies according to the position of piston 40 within cylindrical bore 32 so that the volume of the variable volume container 33 is defined between an end of the piston 40 and the end 34 of the cylindrical bore 32. Piston assembly 38 is preferably of stainless steel. Piston assembly 38 also includes a retaining collar 42 from which piston 40 extends, and an extension 44 extending along the length of rearward region 14 and past base end 8 of body 4. The outer end 46 of extension is knurled and is secured to a hollow cap 48, such as with an adhesive. Cap 48 has a cylindrical skirt 50 which lies adjacent cylindrical outer surface 52 of body 4.

Piston assembly 38, and cap 48 therewith, is biased towards the rest or discharged position of FIG. 3 by a coil spring 54 captured between retaining collar 42 and an end plug 56, end plug 56 being secured to base end 8 of body 4, such as with an adhesive. The axial movement of piston assembly 38 is limited by the contact of retaining collar 42 against an opposed surface 58 of housing 26, shown in FIG. 5, and the end 60 of a sleeve extension 62 of end plug 56. The axial distance travelled of piston assembly 38 is somewhat greater than the 10 mm stroke provided by cylinder assembly 24 to permit the liquid inhalant 64 to fill variable volume container 33. This is discussed in more detail below.

A resilient arm 66 extends from collar 42 and has a natural radially outward bias. When piston assembly 38 is in the discharged position of FIG. 3, arm 66 passes through an opening 68 formed between housing 26 and a catch 70. See FIG. 7. When cap 48 is drawn back by the user to the retracted position of FIG. 5, the end 72 of arm 66 passes through opening 68 and becomes lodged against the opposed surface 74 of catch 70. This outward radial movement of arm 66 also moves a radially movable trigger or button 75 mounted body 4 adjacent catch 70. This radial displacement is shown in FIGS. 3 and 5.

Inhaler 2 includes an axially extending, annular reservoir 76 filled with liquid inhalant 64. Reservoir 76 is defined within region 14 between the inner wall 78 of body 4 and the outer wall 80 of a separating sleeve 82. Separating sleeve 82 is an integral extension of housing 26 and extends between end plug 56 at base end 8 and the beginning 84 of forward region 12 of interior 10. Sleeve 82 not only helps define reservoir 76, it also helps to guide retaining collar 42 and coil spring 54. As illustrated best in FIGS. 5 and 7, reservoir 76 is connected to variable volume container 33 through a pathway 86 formed axially between housing 26 and body 4, and radially through housing 26. Pathway 86 opens up into a circumferential groove 87 and a radially extending bore 88 formed in a sleeve segment 90 positioned between first O-ring 36 and a second O-ring 92. Liquid 64 within reservoir 76 is urged into cylinder 32, as suggested by arrows 94, 95, and 96 in FIG. 5, through a relatively light pressure exerted by a ring seal 98, a separator 100 and a second coil spring 102. Coil spring 102 need not exert a very strong force against liquid 64 since drawing piston 40 from the at-rest or discharged position of FIG. 3 to the retracted position of FIG. 5 creates a partial vacuum within variable volume container 33, which liquid 64 rushes in to fill. Second O-ring 92 helps prevent any leakage of liquid 64 down into the interior of separating sleeve 82.

Pressing button 75 from the extended position of FIG. 5 to the depressed position of FIG. 3 causes end 72 of arm 66 to disengage from catch 70 to permit spring 54 to drive piston assembly 38 towards tip 6. The initial movement of piston 40 first substantially seals pathway 86 and then effectively seals variable volume container 33 once piston 40 contacts first O-ring 36. Liquid 64 within variable volume container 33 then becomes pressurized due the force of spring 54. This pressurized liquid is forced through a slit 104 formed in barrier 22.

Inhaler 2, in particular, barrier 22, cylinder assembly 24 and piston assembly 38, has been designed to atomize liquid inhalant 64 to be in an effective therapeutic range. This range is generally considered to include only very fine drops or a mixture of fine and very fine drops. When the invention is used for other purposes, the range of drop sizes may vary. The use of a slit, in which substantially no material is removed from barrier, is designed to atomize liquid 64 to the desired sized drops, that is, fine drops (10–100 microns) and/or preferably very fine drops (under 10 microns). Note that the effective stroke provided by cylinder assembly starts following first O ring 36 and ends where the outer end of piston 40 comes to rest. The elastomeric barrier is, in the preferred embodiment, formed from a hydrophobic material, silicone rubber, having a durometer hardness of 35 to 50. Barrier 22 has a diameter of 6.35 mm and a thickness of 1.65 mm in its uncompressed state. Slit 104 is centered within barrier 22 and has a length of about 1 mm. Elastomeric barrier 22 in the preferred embodiment is axially deformed slightly so that its thickness is compressed about 15% to create a central raised dome region 106 surrounding slit 104. With the preferred embodiment, most of the components can be made of a suitable plastic, such as polycarbonate or polypropylene. Springs 54, 66 and 102 are preferably metal while piston assembly 38 is preferably stainless steel. O-rings 36, 92 are of a medicinal compatible elastomeric material, such as silicone. Spring 54, in the preferred embodiment, provides a force of about 2.7 kilograms to piston assembly 38.

In use, inhaler 2 is normally maintained in the rest or discharged position of FIG. 3. To prepare inhaler 2 for use, user grasps cap 48 and pulls it to the retracted position of FIG. 5 against the force of spring 54. As piston 40 is retracted within the cylindrical bore 32 the volume of the variable volume container 33 increases. At the retracted position, arm 66 springs outwardly to engage surface 74 of catch 70 and temporarily keeps piston assembly in the retracted position. Simultaneously, liquid 64 rushes into variable volume container 33 along pathway 86, into groove 87 and through bore 88. When ready to use, the user depresses button 75 permitting plunger assembly 38 to raise the pressure of liquid 64 within cylinder 32 causing the liquid to be dispersed through slit 104, atomizing as it does so to a fine and/or very fine drop size.

Inhaler 2 as shown is a disposable device. However, inhaler 2 could be easily modified to make it refillable. Doing so may, however, require some changes in the types of materials for certain components to accommodate wear or contamination. Inhaler 2 is shown in a straight, tubular configuration. If desired, inhaler 2 could be made L-shaped. One way of doing so would be to provide a right-angle pathway at end 34 of cylinder 32, with elastomeric barrier 22 at the end of the right-angle pathway. If it is desired to ensure no air is left within variable volume container 33 before pressing button 75, a sealable bleed hole could be provided at end 34 of cylinder 32. The driving force for piston 40 could be provided in other manners than that shown. For example, piston assembly 28 could be powered by a carbon dioxide cartridge. Slit 104 is shown straight. It may be possible to use other shaped slits as well.

In some situations it may be desired to modify the dispersal pattern of inhaler 2. FIGS. 8–11 illustrate the tip 110 of an alternative embodiment of inhaler 2, the remainder of inhaler 112 being the same as inhaler 2. Tip 110 includes buttons 114, 116 reciprocally mounted within bores 118, 120 opposite the circumference of elastomeric barrier 22. FIG. 8 shows a normal dispersal pattern 122 with neither button 114, 116 depressed. It should be noted that the opening 124 in slit 104 has been greatly enlarged from what is expected to occur for sake of illustration. FIGS. 9 and 10 illustrate tip 110 with buttons 116, 114 depressed to Create deflected dispersal patterns 124, 126. FIG. 11 illustrates a narrowed dispersal pattern 128 with both buttons 114, 116 depressed. If desired, a different number of buttons 114, 116 could be used to modify the dispersal pattern. Other methods of deflection or constriction of elastomeric barrier 22 could be used as well.

Other modifications and variations may be made to the disclosed embodiments without departing from the subject of the invention as defined in the following claims.

What is claimed is:

1. An atomizer for atomizing a liquid comprising:

a body;

an elastomeric barrier mounted to the body, the barrier having outer and inner surfaces and a slit formed therethrough to provide restricted fluid communication between the inner and outer surfaces, the outer surface facing the ambient environment;

a supply of the liquid to be atomized housed within the body;

a cylinder, housed within the body, fluidly coupled to the supply of liquid and opening onto the inner surface of the barrier, the cylinder housing a dose of the liquid to be atomized; and a piston mounted within the body, in direct contact with the dose of the liquid in the cylinder, for reciprocal movement within the cylinder between a retracted position, at least partially withdrawn from the cylinder, and a discharged position, substantially within the cylinder, wherein the piston applies direct pressure on the dose of the liquid in the cylinder to force the liquid through the slit so that the liquid is atomized.

2. The atomizer of claim 1 further including a spring, coupled to the piston, for biasing the piston from the retracted position to the discharged position.

3. The atomizer of claim 2 wherein the body includes a tip end and a base end, the barrier mounted to the tip end, the atomizer further including a cap slidably mounted to the body at the base end; and means for connecting the cap to the piston, so that moving the cap moves the piston therewith.

4. The atomizer of claim 2 further including maintaining means for selectively maintaining the piston in the retracted position, the maintaining means including an outwardly biased resilient arm having an end, a catch positioned to engage the end of the arm when the piston is at the retracted position, and a trigger, manipulatable by a user, for deflecting the end of the arm away from the catch to permit the spring to force the piston to the discharged position.

5. The atomizer of claim 1 wherein the elastomeric barrier is of a hydrophobic material.

6. The atomizer of claim 1 wherein the elastomeric barrier has a durometer hardness of about 35 to 50.

7. The atomizer of claim 1 wherein the elastomeric barrier is of silicone rubber.

8. The atomizer of claim 1 wherein the elastomeric barrier has a natural, uncompressed thickness of about 1.65 mm.

9. The atomizer of claim 1 wherein the slit in the elastomeric barrier is about 1.0 mm long.

10. The atomizer of claim 1 wherein the barrier means is configured so the liquid is atomized into drops no greater than about 100 microns in diameter.

11. The atomizer of claim 1 further comprising means for modifying any liquid dispersal pattern of the liquid forced through the slit.

12. An atomizer for atomizing a liquid comprising:

a body having a tip end and a base end;

an elastomeric barrier mounted to the body, the barrier having outer and inner surfaces and a slit formed therethrough to provide restricted fluid communication between the inside and outside surfaces, the outside surface facing the ambient environment; and pressure means for providing the liquid to the inside surface at an elevated pressure so to force the liquid through the slit, the barrier configured so the liquid is atomized as it passes into the ambient environment, the pressure means including:

a cylinder, housed within the body, opening onto the inner surface of the barrier;

a piston mounted within the body for reciprocal movement within the cylinder between a retracted position, at least partially withdrawn from the cylinder, and a discharged position, substantially within the cylinder;

a spring, coupled to the piston, for biasing the piston from the retracted position to the discharged position;

a cap slidably mounted to the body at the base end;

means for connecting the cap to the piston, so that moving the cap moves the piston therewith; and maintaining means for selectively maintaining the piston in the retracted position, the maintaining means including an outwardly biased resilient arm having an end, a catch positioned to engage the end of the arm when the piston is at the retracted position, and a trigger, manipulable by a user, for deflecting the end of the arm away from the catch to permit the spring to force the piston to the discharged position;

the body including an axially extending annular reservoir for the liquid to be atomized in fluid communication with the cylinder when the piston is in the retracted position; and means for urging the liquid in the reservoir into the cylinder, the urging means including an axially movable ring seal mounted within the axially extending annular reservoir and a coil spring biasing the ring seal along the annular reservoir.

13. An atomizer for atomizing a liquid comprising:

a body;

an elastomeric barrier mounted to the body, the barrier having outer and inner surfaces and a slit formed therethrough to provide restricted fluid communication between the inner and outer surfaces, the outer surface facing the ambient environment;

pressure means for providing the liquid to the inner surface at an elevated pressure so to force the liquid through the slit, the barrier configured so the liquid is atomized as it passes into the ambient environment, wherein the pressure means includes:

a cylinder, housed within the body, opening onto the inner surface of the barrier; and a piston mounted within the body for reciprocal movement within the cylinder between a retracted position, at least partially withdrawn from the cylinder, and a discharged position, substantially within the cylinder;

wherein the body includes an axially extending annular reservoir for the liquid to be atomized in fluid communication with the cylinder when the piston is in the retracted position; and, means for urging the liquid in the reservoir into the cylinder, the urging means including an axially movable ring seal mounted within the axially extending annular reservoir and a coil spring biasing the ring seal along the annular reservoir.

14. A method of atomizing a liquid comprising the steps of:

providing a body and a cylinder housed within the body, the cylinder housing a dose of the liquid to be atomized providing an elastomeric barrier;

fluidly coupling the dose of liquid within the cylinder to an inner surface of an elastomeric barrier having an outer surface facing an ambient environment and a slit formed therethrough to provide restricted fluid communication between the inner and outer surfaces providing a piston;;

moving a piston from a retracted position, at least partially withdrawn from the cylinder, to a discharged position, substantially within the cylinder; and driving at least a portion of the dose of liquid in the cylinder through the slit formed in the elastomeric barrier from the inner surface to the outer surface and atomizing the liquid.

15. The method of claim 14 further comprising the steps re-filling the cylinder with the liquid from a liquid reservoir after the moving step; and preventing flow of the liquid from the cylinder to the liquid reservoir during at least a portion of the time during the moving step.

\* \* \* \* \*